(12) United States Patent
Awaad et al.

(10) Patent No.: US 9,533,019 B1
(45) Date of Patent: Jan. 3, 2017

(54) CALOTROPIS PROCERA EXTRACTS AS ANTI-ULCERATIVE COLITIS AGENTS

(71) Applicant: KING SAUD UNIVERSITY, Riyadh (SA)

(72) Inventors: Amani Shafeek Awaad, Riyadh (SA); Ghada Mohamed Zain, Riyadh (SA); Reham M. El-Meligy, Riyadh (SA); Haya Fahd Alkanhal, Alkharj (SA); Vidya Devenathadesikan Seshadri, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/059,261

(22) Filed: Mar. 2, 2016

(51) Int. Cl.
*A61K 36/27* (2006.01)
*A61K 36/185* (2006.01)

(52) U.S. Cl.
CPC ......... *A61K 36/185* (2013.01); *A61K 2236/33* (2013.01)

(58) Field of Classification Search
CPC ..................................................... A61K 36/27
USPC ........................................................ 424/725
See application file for complete search history.

(56) References Cited

U.S. PATENT DOCUMENTS

| | | | | |
|---|---|---|---|---|
| 2004/0082521 A1* | 4/2004 | Singh | ................... | A61K 9/1271 514/26 |
| 2006/0057237 A1* | 3/2006 | Darro | ..................... | A61K 36/27 424/777 |
| 2008/0280995 A1 | 11/2008 | Kumar et al. | | |
| 2012/0177730 A1* | 7/2012 | Baron | .................. | A61K 9/2054 424/452 |
| 2014/0271863 A1* | 9/2014 | Anderson | .............. | A61K 47/32 424/486 |

OTHER PUBLICATIONS

Pandey et al., "Invitro Assesment of Antibacterial Activity of Calotropis Procera and Coriandrum Sativum Against Various Pathogens," *Int. J. of Pharm. Res. & All. Sci.*, 2015, vol. 4, pp. 33-44.

\* cited by examiner

*Primary Examiner* — Chris R Tate

(74) *Attorney, Agent, or Firm* — Richard C. Litman

(57) ABSTRACT

The *Calotropis Procera* extracts as anti-ulcerative colitis agents include extracts of *Calotropis procera* obtained by a method comprising the following steps: (a) providing a plant material derived from *Calotropis procera*, (b) drying the plant material, (c) pulverizing the plant material to provide a fine powder; and (d) extracting the plant material by percolation using 95% aqueous alcohol in a container to obtain an alcoholic extract. A method of treating ulcerative colitis comprises administering a therapeutically effective amount of an alcoholic extract of *C. procera* to a patient in need thereof.

2 Claims, 1 Drawing Sheet

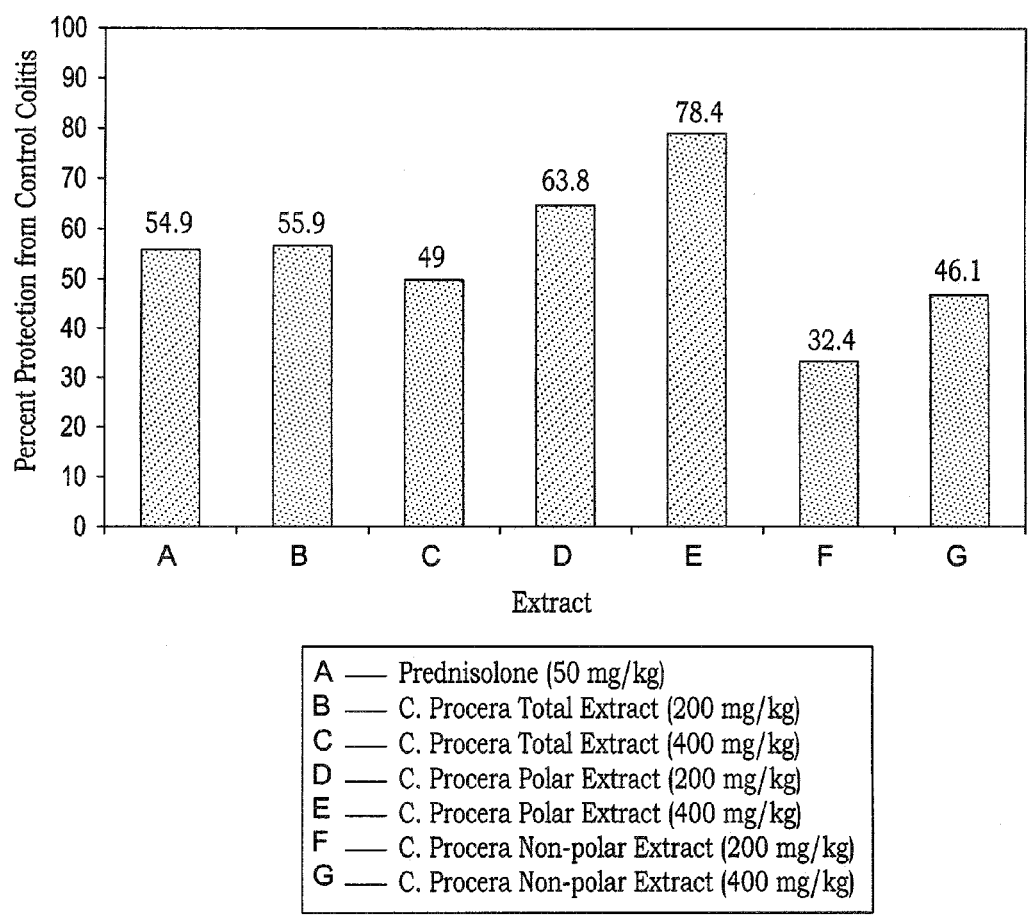

CALOTROPIS PROCERA EXTRACTS AS ANTI-ULCERATIVE COLITIS AGENTS

BACKGROUND OF THE INVENTION

1. Field of the Invention

The present invention relates to traditional medicinal plant extracts, and particularly to *Calotropis Procera* extracts as anti-ulcerative colitis agents useful for the treatment of ulcerative colitis.

2. Description of the Related Art

*Calotropis procera* is a wild growing plant of the Asclepiadaceae family. Different parts of the plant are used in the treatment of various diseases in folk medicine, and their effects were confirmed by scientific experiments. Various studies have demonstrated biological activities of *C. procera*. There are reports of inflammatory responses, analgesic, anti-microbial larvicides, nematicides, anticancer, and weak antipyretic activities. There are also studies of contraceptive activities reported in rats. In addition, this plant showed potential hepatoprotective, antioxidant, and antibacterial activities.

Ulcerative colitis (UC) is an inflammatory bowel disease that primarily affects the colonic mucosa and sub-mucosa. The most common symptoms of UC are ulcers and inflammation of the inner lining of the colon that lead to symptoms of bloody diarrhea, passage of pus, mucus, and abdominal cramping during bowel movements. Currently, there is no effective therapy to cure the disease, but the mainstream treatment depends on the reduction of the symptoms. The treatment depends on the severity of the disease. Therefore, treatment is adjusted for each individual.

In the discovery of new anti-ulcerogenic drugs, special interest has been directed to natural plant products based upon traditional medicine (TM). Therapies based on natural products (plants & herbs) derived from TM have proved to be clinically effective and relatively less toxic than existing pharmaceutical drugs because they reduce the offensive side effects of pharmaceutical drugs.

Thus, extracts of *Calotropis Procera* extracts as anti-ulcerative colitis agents solving the aforementioned problems are desired.

SUMMARY OF THE INVENTION

The *Calotropis Procera* extracts as anti-ulcerative colitis agents include extracts of *Calotropis procera* obtained by a method comprising the following steps: (a) providing a plant material derived from *Calotropis procera*, (b) drying the plant material, (c) pulverizing the plant material to provide a fine powder; and (d) extracting the plant material by percolation using 95% aqueous alcohol in a container to obtain an alcoholic extract. The method may further comprise (e) optionally repeating step (d) at least one additional time to obtain additional alcoholic extract; (f) filtering the alcoholic extract; and (g) concentrating the crude alcoholic extract to obtain a solid extract. The method may additionally comprise (h) suspending the solid extract obtained in step (g) in water to form a mixture; (i) filtering the mixture; (j) isolating a solid, non-polar extract on the filter and an aqueous filtrate; and (k) optionally concentrating the aqueous filtrate to obtain a solid, polar extract.

A method of treating ulcerative colitis comprises administering a therapeutically effective amount of an alcoholic extract of *C. procera* to a patient in need thereof.

Surprisingly, the polar extract derived from *Calotropis procera* displayed potent anti-ulcerative colitis activity in a dose-dependent manner and was found to be more effective than the standard drug Prednisolone in a subject mammal.

These and other features of the present invention will become readily apparent upon further review of the following specification.

BRIEF DESCRIPTION OF THE DRAWINGS

The sole drawing FIGURE is a chart comparing treatment of acetic acid-induced colitis in male Wistar rats by prednisolone with various *Calotropis Procera* extracts.

DETAILED DESCRIPTION OF THE PREFERRED EMBODIMENTS

The *Calotropis Procera* extracts as anti-ulcerative colitis agents relates to extracts of the plant *Calotropis procera* having a pharmacological activity, in particular, an anti-ulcerative colitis activity.

An extract of *Calotropis procera* is obtained by a method comprising the following steps: (a) providing a plant material derived from *Calotropis procera*, (b) drying the plant material, (c) pulverizing the plant material to provide a fine powder; and (d) extracting the plant material by percolation using 95% aqueous alcohol in a container to obtain an alcoholic extract. The method may further comprise (e) optionally repeating step (d) at least one additional time to obtain additional alcoholic extract; (f) filtering the alcoholic extract; and (g) concentrating the crude alcoholic extract to obtain a solid extract. The method may additionally comprise (h) suspending the solid extract obtained in step (g) in water to form a mixture; (i) filtering the mixture; (j) isolating a solid, non-polar extract on the filter and an aqueous filtrate; and (k) optionally concentrating the aqueous filtrate to obtain a solid, polar extract.

The plant material for preparing the extract consists of the aerial parts of *Calotropis procera*. The extract of *Calotropis procera* can be concentrated under reduced pressure at room temperature. During the percolation step, the container can be agitated to improve the extraction of the active agents from the *Calotropis procera* plant. The percolation may be carried out for about 72 hours. The extract of *Calotropis procera* may be dried in air and/or in shade. Typically, the extract is filtered using filter paper or cotton to isolate the solid particles.

A method of treating ulcerative colitis comprises administering a therapeutically effective amount of an extract of *Calotropis procera* to a patient in need thereof.

A therapeutically effective amount of the extract or an amount effective to treat or prevent ulcerative colitis may be determined initially from in vivo studies described herein. For example, an effective amount of the total alcohol, polar and non-polar extract can be about 200-400 mg/kg.

The present technology, thus generally described, will be understood more readily by reference to the following examples, which are provided by way of illustration.

Example 1

Preparation of *Calotropis procera* Extract

The aerial part of *Calotropis procera* were collected during flowering stage from Al-Yamamah territory (Al-Kharj. South of Riyadh KSA). Plant material was air-dried in shade, pulverized to fine powder, refilled in tightly closed containers and stored for photochemical and pharmacological studies. The air dried powders (~250 g) of *Calotropis*

*procera* were extracted by percolation in 95% aqueous ethanol with occasional agitation for about 72 h. The ethanol extract were filtered using standard filter paper, and the residues were re-percolated three times. The combined filtrates were concentrated under reduced pressure at low temperature to yield about 85 g (total alcohol extract). The residues obtained were suspended in about 300 mL water, and then filtered over a piece of cotton or filter paper. The materials obtained on the top of the cotton piece were non-polar components, termed "non-polar extract" while the filtrate included the polar components, and is termed the "polar extract."

For determination of the active constituents, the air dried powders of the investigated plant (*Calotropis procera*) were subjected to preliminary phytochemical screening according to the published methods. For determination of the pharmacological studies, Swiss albino mice of both sex (26-30 g) and male Wistar rats (180-200 g) were purchased from the animal house of King Saud University, KSA. Animals were housed in standard polypropylene cages with wire mesh top and maintained under standard conditions (temperature 23±1.0° C., humidity 55±10%, 12 h light/12 h dark cycle). They were fed with a standard pellet diet with water ad libitum and were allowed to adapt to the laboratory environment for one week before experimentation. The total ethanol extract of *Calotropis procera* was freshly suspended in distilled water just before administration to the experimental subjects by the aid of Tween 80.

Example 2

Determination of Acute Toxicity ($LD_{50}$) on Swiss Albino Mice

The oral median lethal dose ($LD_{50}$) of the total alcohol extract of *Calotropis procera* was determined as described by Lorke (1983). Swiss albino mice in groups of six, received one of 500, 1000, 2000, or 4000 mg/kg doses of the tested extract. Control animals received the vehicle only while being kept under the same conditions. Signs of acute toxicity and number of deaths per dose within 24 h were recorded.

Example 3

Determination of Acute Toxicity ($LD_{50}$) on Wistar Rats

Wistar rats were randomly divided into two groups each of 10 animals. Rats of the first group received the vehicle in a dose of 5 mL/kg and were left as normal control. Rats of the second group were administered the total alcohol extract of *Calotropis procera* (400 mg/kg). All medications were administered orally daily for 35 consecutive days. Animals were maintained under identical conditions with food and water ad libitum for the entire period with close observation. At the end of the experimental period, blood samples (about 2 mL) were drawn by puncturing the retro-orbital venous sinus of each rat under ether anesthesia and centrifuged at 10,000 rpm for 5 minutes. The sera were separated to be used for the biochemical estimations. Liver functions were evaluated by measuring the serum activity of alanine aminotransferase (ALT), aspartate aminotransferase (AST), albumin and total proteins. Serum levels of urea, total bilirubin and creatinine were determined as measures of kidney functions for the total alcohol extract.

Example 4

Effect on Ulcerative Colitis

Male Wistar rats were divided into 9 experimental groups, each of 6 animals. Rats of groups 1 and 2 received the vehicle (5 mL/kg) and served as normal control and control colitis groups, and Group 3 was administered dexamethasone (0.1 mg/kg) and served as Reference Drug group. The alcohol extract, polar extract and non-polar extract of *Calotropis procera* were administrated at doses of 200 mg/kg to rats of groups 4, 5 and 6 and at doses of 400 mg/kg to rats of groups 7, 8 and 9, respectively. All medications were administered orally, once daily for 5 consecutive days after colitis induction. The first doses were administrated in all groups one hour after colitis induction. The colonic lesions were assessed by weighing the colon specimens and the wet weight/length ratio was calculated for all the rats. The specimens were examined under a dissecting microscope and the lesion scores were quantified by scoring system (0-5). Ulcer area was measured using a plane glass square. Each cell on the glass square was 1 $mm^2$ in area, and the number of cells was counted and the ulcer area was determined for each colon.

The Ulcer index (UI) was measured by summing the lesion score and the ulcer area for each colon specimen. The curative ratio was determined according to formula (1) below:

$$\text{Curative Ratio} = \frac{\text{Control } UI - \text{Test } UI}{\text{Control } UI} \times 100 \quad (1)$$

Preliminary phytochemical screening of *Calotropis procera* showed that it contains unsaturated sterols and/or triterpenoids, flavonoids, cardiac glycosides, carbohydrates or glycosides, proteins and/or amino acids, tannins and coumarins.

The pharmacological activity of the tested extract is characterized by a low degree of toxicity. The obtained results indicated that various doses of the alcohol *Calotropis procera* extract ranging from 500, 1000, 2000 up to 4000 mg/kg did not produce any symptom of acute toxicity, and none of the mice died during 24 h of observation. It was suggested that oral $LD_{50}$ of the tested extracts were higher than 4000 mg/kg, and the tested extract is considered safe.

The non-toxic nature of the alcohol extract of *Calotropis procera* in acute toxicity study is well supported by the results of sub-chronic toxicity study. Oral dosing of *Calotropis procera* alcohol extract (400 mg/kg) for 35 days did not show any significant effect on the levels of ALT, AST, total bilirubin, total proteins, albumin, urea and creatinine in their sera as compared to control non-treated rats (Table 1). Alcohol extract of *Calotropis procera* (400 mg/kg) was administrated to rats for 35 days, n=10, sera were collected, and activity of different enzymes was measured.

TABLE 1

Effect of Alcohol Extract of
*Calotropis procera* on Liver and Kidney Functions

| Parameter | Normal Control | Total alcohol extract |
|---|---|---|
| ALT (U/L) | 67.50 ± 3.48 | 69.3 ± 2.73 |
| AST (U/L) | 146.30 ± 5.20 | 160.4 ± 6.54 |
| Total bilirubin (mg/dL) | 1.70 ± 0.11 | 1.73 ± 0.10 |

TABLE 1-continued

Effect of Alcohol Extract of
*Calotropis procera* on Liver and Kidney Functions

| Parameter | Normal Control | Total alcohol extract |
|---|---|---|
| Total protein (g/dL) | 8.65 ± 0.22 | 8.35 ± 0.34 |
| Albumin (g/dL) | 3.72 ± 0.01 | 3.20 ± 0.25 |
| Urea (mg/dL) | 37.00 ± 2.35 | 38.05 ± 2.55 |
| Creatinine (mg/dL) | 0.43 ± 0.22 | 0.40 ± 0.25 |

The model of acetic acid induced colitis shares many of the histologic features of ulcerative colitis in human beings, including mucosal edema and submucosal ulceration.

In rats of normal control group, no abnormal changes were observed, suggesting that the handling procedure had no interference with the experimental outputs. Macroscopic damage parameters of the colon of control colitis rats two days after rectal infusion of acetic acid revealed dark brown lesions, mucosal hyperemia, edema, erosion, and ulceration. Control colitis rats showed lesion score, ulcer area and ulcer index values of 4.7±0.29, 5.5±0.34 cm2 and 10.2±0.63, respectively are provided in Table 2.

TABLE 2

Effects of *Calotropis procera* extracts

| Groups | Lesion score (0-5) | Ulcer area (cm$^2$) | Ulcer index | Wet W/L (g/cm) |
|---|---|---|---|---|
| Normal control | 0.0 ± 0.0 | 0.0 ± 0.0 | 0.0 ± 0.0 | 0.34 ± 0.03 |
| Control colitis | 4.71 ± 0.29 | 5.55 ± 0.34 | 10.20 ± 0.63 | 0.98 ± 0.07 |
| Prednisolone (50 mg/kg) | 2.22 ± 0.12* | 2.53 ± 0.15* | 4.65 ± 0.27* | 0.46 ± 0.02* |
| C. procera total extract (200 mg/kg) | 2.50 ± 0.23* | 3.80 ± 0.30* | 4.55 ± 0.43* | 0.56 ± 0.05* |
| C. procera total extract (400 mg/kg) | 1.91 ± 0.15* | 2.50 ± 0.27* | 5.20 ± 0.34* | 0.48 ± 0.05* |
| C. procera polar extract (200 mg/kg) | 1.50 ± 0.19* | 2.00 ± 0.28* | 3.50 ± 0.31* | 0.53 ± 0.06* |
| C. procera polar extract (400 mg/kg) | 1.35 ± 0.20* | 1.65 ± 0.25* | 2.50 ± 0.27* | 0.42 ± 0.04* |
| C. procera non-polar extract (200 mg/kg) | 3.35 ± 0.27* | 3.65 ± 0.27* | 6.92 ± 0.39* | 0.55 ± 0.04* |
| C. procera non-polar extract (400 mg/kg) | 3.00 ± 0.24* | 2.40 ± 0.23* | 5.50 ± 0.27* | 0.62 ± 0.05* |

*Significantly different from the control colitis at, $p < 0.05$.

The inflammatory changes of the intestinal tract were associated with a significant increase of wet weight/length of the colon specimens as an indicator of inflammation. These inflammatory indices were significantly improved by oral dosing of Prednisolone, alcohol, polar and non-polar extracts of *Calotropis procera* and for 5 days after colitis induction. As shown in the FIGURE. The FIGURE shows the effect of investigated extracts on acetic acid-induced colitis in rats. The FIGURE shows % protection of control colitis for 7 groups of animals (n=6), treated with alcohol, polar & non-polar extracts of *Calotropis procera* (200 and 400 mg/kg) and Prednisolone (50 mg/kg) for 5 successive days after ulcerative colitis induction. The colitis was induced by slowly infusion of 2 mL (4%, v/v) acetic acid in saline into the colon through the catheter.

All the investigated extracts possessed dose-dependent anti-ulcerative colitis potentials. They reduced different parameters of ulcerative colitis, as shown in Table 1. Only the polar extract at both doses of 200 mg/kg and 400 mg/kg was more effective than Prednisolone administered at 50 mg/kg). The administered doses produced percent protection of control colitis by 63.8% and 78.4%, respectively, while the standard drug Prednisolone produced 54.9% protection. The total alcohol extract was safe up to 4000 mg/kg, and there were no side effects reported on liver and kidney functions.

*Calotropis Procera* different extracts possessed potent anti-ulcerative colitis activity in a dose dependent matter, where the polar extract was the most effective one and was more effective than the standard drug Prednisolone. This is surprising and unexpected result based on the fact that it is more effective than the standard drug Prednisolone in a subject mammal. The anti-ulcerative colitis activity may be attributed to the bioactive principles, namely, the flavonoids present in the *Calotropis Procera* plant.

The total alcohol extract was found to be safe up to 4000 mg/kg, and there were no side effects reported on liver and kidney functions.

It is to be understood that the present invention is not limited to the embodiments described above, but encompasses any and all embodiments within the scope of the following claims.

We claim:

1. A method of treating ulcerative colitis, comprising the step of administering a therapeutically effective amount of an alcoholic extract to a patient in need thereof, wherein the therapeutically effective amount is at least 200 mg/kg daily.

2. The method of treating ulcerative colitis according to claim 1, wherein the therapeutically effective amount is at least 400 mg/kg daily.

* * * * *

UNITED STATES PATENT AND TRADEMARK OFFICE
CERTIFICATE OF CORRECTION

| | | |
|---|---|---|
| PATENT NO. | : 9,533,019 B1 | Page 1 of 1 |
| APPLICATION NO. | : 15/059261 | |
| DATED | : January 3, 2017 | |
| INVENTOR(S) | : Amani Shafeek Awaad et al. | |

It is certified that error appears in the above-identified patent and that said Letters Patent is hereby corrected as shown below:

Column 6, Lines 43-46, cancel the entire Claim 1 and insert the following claim:
-- 1. A method of treating ulcerative colitis, comprising the step of administering a therapeutically effective amount of an alcoholic extract of *Calotropis procera* to a patient in need thereof, wherein the extract of *Calotropis procera* is a polar extract, further wherein the therapeutically effective amount is at least 200 mg/kg daily. --

Signed and Sealed this
Twenty-seventh Day of November, 2018

Andrei Iancu
*Director of the United States Patent and Trademark Office*